US011076760B2

(12) United States Patent
Dreher

(10) Patent No.: US 11,076,760 B2
(45) Date of Patent: Aug. 3, 2021

(54) APPARATUS CONFIGURATED TO AND A PROCESS TO PHOTOACOUSTICALL IMAGE AND MEASURE A STRUCTURE AT THE HUMAN EYE FUNDUS

(71) Applicant: LEGALINE AG, Walchill (CH)

(72) Inventor: Andreas W. Dreher, Escondido, CA (US)

(73) Assignee: LEGALINE AG, Walchill (CH)

(*) Notice: Subject to any disclaimer, the term of this patent is extended or adjusted under 35 U.S.C. 154(b) by 572 days.

(21) Appl. No.: 14/785,923

(22) PCT Filed: May 7, 2014

(86) PCT No.: PCT/EP2014/059396
§ 371 (c)(1),
(2) Date: Oct. 21, 2015

(87) PCT Pub. No.: WO2014/180932
PCT Pub. Date: Nov. 13, 2014

(65) Prior Publication Data
US 2016/0081556 A1 Mar. 24, 2016
US 2016/0374564 A9 Dec. 29, 2016

Related U.S. Application Data

(63) Continuation of application No. PCT/EP2014/059396, filed on May 7, 2014.
(Continued)

(51) Int. Cl.
*A61B 5/00* (2006.01)
*A61B 3/12* (2006.01)
(Continued)

(52) U.S. Cl.
CPC .......... *A61B 5/0095* (2013.01); *A61B 3/0008* (2013.01); *A61B 3/0025* (2013.01);
(Continued)

(58) Field of Classification Search
CPC .............. A61B 5/0095; A61B 5/14532; A61B 5/14546; A61B 5/6821; A61B 3/0008;
(Continued)

(56) References Cited

U.S. PATENT DOCUMENTS 5,116,114 A * 5/1992 Nakamura ............. A61B 3/152
351/205
6,830,567 B2 * 12/2004 Schuele ............... A61B 5/0095
128/898
(Continued)

OTHER PUBLICATIONS

International Search Report and Written Opinion dated Jul. 22, 2014 in PCT/EP2014/059396 Filed May 7, 2014.

*Primary Examiner* — Joanne M Hoffman
(74) *Attorney, Agent, or Firm* — Global IP Counselors, LLP

(57) ABSTRACT

An apparatus configured to photoacoustically image and measure a structure at the human eye fundus or components, substances, cells, tissue, or analytes within the eye and within the blood vessels of the eye including an emitter element for emitting electro-magnetic radiation, a transition element for delivering the electro-magnetic radiation into an eye, a detection element for detecting an acoustic wave and converting the acoustic wave into a digital wave signal, an analysis element for processing the digital wave signal into an image or measurement or both, and a display element for displaying a representation of the image and/or the measurement. The apparatus additionally includes a coupling member, the coupling member being configured and arranged to acoustically couple the eye to the detection element such that the acoustic wave generated within the eye can be guided onto the detection element.

26 Claims, 16 Drawing Sheets

Related U.S. Application Data

(60) Provisional application No. 61/855,248, filed on May 13, 2013.

(51) Int. Cl.
*A61B 5/145* (2006.01)
*A61B 3/10* (2006.01)
*A61B 3/00* (2006.01)

(52) U.S. Cl.
CPC .............. *A61B 3/0041* (2013.01); *A61B 3/10* (2013.01); *A61B 3/12* (2013.01); *A61B 5/004* (2013.01); *A61B 5/0036* (2018.08); *A61B 5/14532* (2013.01); *A61B 5/14546* (2013.01); *A61B 5/4887* (2013.01); *A61B 5/6821* (2013.01); *A61B 5/7289* (2013.01); *A61B 5/14542* (2013.01); *A61B 2560/0425* (2013.01); *A61B 2562/028* (2013.01); *A61B 2576/02* (2013.01)

(58) Field of Classification Search
CPC ....... A61B 3/0083; A61B 3/13; A61B 3/0025; A61B 3/0041; A61B 3/12; A61B 2560/0425; A61B 2560/028; A61B 2560/02
See application file for complete search history.

(56) References Cited

U.S. PATENT DOCUMENTS

| | | | |
|---|---|---|---|
| 8,903,468 B2* | 12/2014 | Peyman | A61F 9/00821 600/407 |
| 9,037,217 B1* | 5/2015 | Peyman | A61B 18/20 600/427 |
| 9,351,879 B2* | 5/2016 | Gooding | A61F 9/009 |
| 2002/0101566 A1* | 8/2002 | Elsner | A61B 3/12 351/200 |
| 2003/0028104 A1* | 2/2003 | Wilson | G10K 11/02 600/437 |
| 2003/0210378 A1* | 11/2003 | Riza | A61B 3/066 351/205 |
| 2004/0080467 A1* | 4/2004 | Chinthammit | G06F 3/011 345/7 |
| 2006/0187462 A1* | 8/2006 | Srinivasan | A61B 3/102 356/479 |
| 2007/0088206 A1* | 4/2007 | Peyman | A61B 5/1455 600/319 |
| 2007/0225574 A1* | 9/2007 | Ueda | A61B 5/00 600/300 |
| 2007/0255141 A1* | 11/2007 | Esenaliev | A61B 5/1075 600/475 |
| 2007/0266791 A1* | 11/2007 | Nakamura | G01S 7/52025 73/627 |
| 2008/0161781 A1* | 7/2008 | McArdle | A61F 9/00802 606/6 |
| 2009/0105605 A1* | 4/2009 | Abreu | A61B 5/0008 600/549 |
| 2010/0016717 A1* | 1/2010 | Dogra | A61B 5/0059 600/437 |
| 2010/0191107 A1* | 7/2010 | Bowers | A61B 5/0091 600/436 |
| 2010/0249562 A1* | 9/2010 | Zhang | A61B 5/0059 600/365 |
| 2012/0004554 A1* | 1/2012 | Aoki | A61B 8/4281 600/459 |
| 2012/0026462 A1* | 2/2012 | Uhlhorn | A61B 3/102 351/206 |
| 2012/0150013 A1* | 6/2012 | Peyman | A61B 5/0095 600/407 |
| 2012/0271204 A1* | 10/2012 | Peyman | A61B 5/0095 601/2 |
| 2013/0102922 A1* | 4/2013 | Gooding | A61B 3/14 600/558 |
| 2013/0103014 A1* | 4/2013 | Gooding | A61B 3/102 606/6 |
| 2013/0104657 A1* | 5/2013 | Lin | G01N 15/02 73/602 |
| 2015/0141972 A1* | 5/2015 | Woodley | A61B 3/102 606/5 |
| 2015/0316510 A1* | 11/2015 | Fukushima | G02B 21/002 73/643 |
| 2015/0335479 A1* | 11/2015 | Shibata | A61F 9/00825 606/5 |
| 2016/0093063 A1* | 3/2016 | Gonzalez | A61B 3/145 382/107 |
| 2016/0331240 A1* | 11/2016 | Leahy | A61B 5/0095 |

* cited by examiner

APPARATUS CONFIGURATED TO AND A PROCESS TO PHOTOACOUSTICALL IMAGE AND MEASURE A STRUCTURE AT THE HUMAN EYE FUNDUS

CROSS-REFERENCE TO RELATED APPLICATIONS

This application is a U.S. National Stage Application of International Application No. PCT/EP2014/059396, filed May 7, 2014, which claims priority to U.S. Provisional Application 61/855,248 filed May 8, 2013, the contents of each of which is hereby incorporation herein by reference.

BACKGROUND

Field of Invention

The invention relates to an apparatus configured to photoacoustically image and measure a structure at the human eye fundus and a process to photoacoustically image and measure structures at the human eye fundus.

The present application generally relates to imaging and measuring structures at the fundus of the human eye and to imaging and measuring components, substances, cells, tissue, or analytes within the eye and within the blood vessels of the eye.

Background Information

In many medical and non-medical applications it is desirable to obtain an image or measurements of the fundus of the eye and its structures. Present principles of ocular imaging are based on illuminating the fundus of an eye with light or other electromagnetic radiation. The signal to be detected includes the light that has been reflected or backscattered from the fundus. However, a large amount of optical noise in the form of undesired reflections is created from the anterior surfaces of the eye, creating challenges in obtaining images or measurements of the fundus with acceptable signal-to-noise ratio.

Photoacoustic imaging is not affected by optical noise or reflections since the signal to be detected is an acoustic wave. Therefore, it is desirable to apply this technology towards imaging and measuring applications of the fundus of the human eye and its structures.

SUMMARY

In many non-medical applications and in the detection and treatment of many diseases it is advantageous to obtain an image or measurements of the fundus of the human eye, in particular of the retina and its layers, the choroid, the retinal blood vessels, the choroidal blood vessels, the fovea, the optic nerve head, and of any components, substances, cells, tissue, or analytes within the blood vessels, vitreous, or aqueous.

Present principles of ocular imaging are based on illuminating an area of interest with light or other electromagnetic radiation, and detecting the amount of light or other electromagnetic radiation reflected or backscattered from the area of interest.

Since the retina is highly efficient in absorbing light in order to generate an optical signal to send to the brain, there is very little light being reflected or backscattered from the retina. Depending on the wavelength of the light impinging onto the retina, only 1% to 3% is reflected or backscattered towards the pupil of the eye, of which a fraction exits through the pupil and can be detected by optical sensors.

At the same time, the amount of light reflected from the anterior segment of the eye, i.e. cornea and lens, is of at least the same magnitude as the light returning from the back of the eye, causing optical noise and reflections in the image or measurement of the retina and its sub-structures. In order to minimize the optical noise and reflections, optical fundus imagers have been using means of aperture stops, separated entrance and exit pupils, polarization filters, optical coherence sensors, confocal detection arrangements, or a combination thereof. Even with the above improvements it remains a significant challenge with optical fundus imagers to align a patient's eye with respect to the fundus imager so as to minimize reflections from the anterior segment, requiring either highly skilled operators or expensive automated alignment systems, or both.

Photoacoustic imaging has been employed for many years in material inspection, detection of trace elements and non-ophthalmic medical imaging applications. A short light or laser pulse is used to illuminate a small area of the sample to be examined. The light pulse is partially absorbed by select substances or molecules in the sample and is released as heat or infrared radiation. The localized generation of heat causes a microscopically small area in the sample to expand causing a pressure wave that travels through the sample with the speed of sound and can be detected with an acoustic transducer.

The amplitude of the acoustic pulse is a measure for the amount of light absorbed by the molecules in the sample; the greater the absorbance the stronger the acoustic pulse signal. This is in contrast to optical imaging where a greater absorbance leads to a weaker optical signal. The time delay between the application of the light pulse and the detection of the acoustic signal is a measure for the distance between the origin of the acoustic pulse and the acoustic detector.

It is desirable to apply this technology towards imaging and measuring applications of the fundus of the human eye and its structures, including the retina and its blood vessels.

One problem in applying photoacoustic technology towards the human eye is that an acoustic sensor has to be coupled to the eye so that the acoustic signal can be detected. Attempts have been made by coupling a water tank containing an acoustic transducer to the cornea of the eye. Other attempts were made by anaesthetizing the cornea and placing an acoustic transducer directly onto the cornea of the eye. None of the attempts offer a practical solution to apply photoacoustic technology towards routine examination or imaging of a living human eye.

An apparatus configured to photoacoustically image and measure structures of the human eye fundus includes an emitter element that emits electro-magnetic radiation, a transition element that delivers the electro-magnetic radiation into an eye, a detection element that detects acoustic waves and converts the acoustic waves into a digital wave signal, a coupling member that acoustically couples the eye to the detection element such that acoustic waves generated within the eye are guided onto the detection element, an analysis element that processes the digital wave signal into images or measurements or both, and a display element that displays a representation of the images and/or measurements.

The apparatus may be embodied as a handheld device which can be self-applied by a patient or a user, or as a stationary device which can be self-applied by a patient or a user, or as a workstation device where an operator applies the apparatus to a patient.

The emitter element may consist of one or more light sources that emit electro-magnetic radiation as beams of different wavelengths, and a beam combiner that combines the beams of different wavelengths into one illumination beam. The light sources may be LEDs, laser diodes, or lasers with different wavelengths, or may be a broadband light source covering a range of wavelengths that is separated sequentially or simultaneously into beams of different wavelengths. The light sources of the emitter element may each be modulated such that the intensity of their respective beams can be varied over time. The modulation may be in the form of one or multiple pulses whereby the pulse start of any one of the light sources may be delayed from the pulse start of the other light sources of the emitter element. A photo detector may be incorporated into the emitter element to monitor the pulse width and/or intensity of the illumination beam.

The transition element guides the illumination beam onto the eye of the patient or user such that said beam travels through the cornea and aqueous, through the pupil, lens, and vitreous onto an area of interest of the eye fundus. The transition element can be defined by one or more optical components arranged between the emitter element and the eye of the patient and may consist of lenses, mirrors, beam scanners, optical fibers, prisms, or combinations thereof. The transition element may guide the illumination beam to one or a plurality of areas of interest.

At each area of interest, one or a multitude of pulses of specific pulse duration and wavelength may be emitted by the emitter element such that the energy transported by the illuminating beam is at least partially absorbed by a structure of the eye or a substance in the eye at the area of interest which directly or indirectly re-emits a part of the absorbed energy in the form of an acoustic wave. The more energy was absorbed, the stronger is the acoustic wave. At each area of interest, additional pulses of beams of different wavelengths may be applied, are absorbed by a different substance, and generate additional acoustic waves. The acoustic waves travel through the eye with the speed of sound which, in water, is approximately 1,500 m/s, and are collected by the coupling member.

The coupling member may be embodied as a tubular structure made of an acoustically conducting material which touches the upper and/or lower eye lids of the patient's eye while the eye is open. The illuminating beam passes through the center of the tubular structure into the eye. The coupling member may be composed of several parts, including an eyelid contact piece and one or more acoustic lenses. The eyelid contact piece may be made of a soft material which is in direct contact with the eye lids of the patient or may be pliable so that it conforms to the shape of the upper and lower eye lids and facial features around the patient's eye in order to offer optimum acoustical contact between the eye lids and the coupling member. The material of the eyelid contact piece may exhibit low attenuation of acoustic waves and acoustic impedance close to that of living tissue. Suitable materials are, for example, cross-linked hydrophilic polymers, elastomeric filled silicone compositions, or filled polyurethane compositions. A coupling gel or fluid may or may not be used between the eyelid contact piece and the patient's eye lids. The eyelid contact piece may be constructed such that it can be removed from the coupling member and replaced and/or disinfected after each use.

Mounted to or within the coupling member is the detection element which may consist of one or a plurality of acoustic sensors capable of detecting acoustic waves with frequencies in the MHz range and one or more acoustic lenses. For example, piezoelectric sensors or transducers may be used as acoustic sensors. The acoustic lenses of the coupling member image or guide the acoustic waves generated by the illuminating beam in the eye and collected by the eyelid contact piece onto the acoustic sensor and may consist of a material exhibiting a gradient acoustic impedance so to match the acoustic impedance of living tissue or the eyelid contact piece at one end and to match the acoustic impedance of the acoustic sensors at the other end. Alternatively, a stack of materials with incrementally changing acoustic impedances may be used.

The detection element converts the detected acoustic waves into electrical wave signals which are amplified, digitized by an analog-to-digital converter (ADC), and transmitted to the analysis element as digitized acoustic wave signals. The analysis element may or may not be a physical part of the apparatus, and the transmission of the digitized acoustic wave signals from the detection element to the analysis element may be made directly or indirectly by wire, storage media, wireless or through the internet. The analysis element may be comprised of a processor programmed to extract measurements from the digitized acoustic wave signal. The measurements may include wave amplitudes, time delays, phase shifts and frequency components 64 of the detected acoustic waves and are used to create the data output of the analysis element.

The peak-to-peak amplitude of the digitized acoustic wave signal are a measure of how much of the illuminating beam was absorbed at the area of interest. Using the known energy of the illuminating beam (pulse length times intensity) for scaling, the data output may consist of a map of digital values where each point in the map corresponds to an area of interest at the eye fundus, and where the digital value relates to the amount of absorbed energy at such area of interest. The digital value may be displayed numerically, or coded by gray scale or color scale.

In one aspect of the invention, the wavelength of the emitter element may be chosen at a wavelength where absorption by the hemoglobin in the blood is at a peak. In this example, the resulting data output map would primarily show high values where a retinal blood vessel was illuminated, and lower values elsewhere. Such a blood vessel map may be used to identify a person based on an individual's unique branching of the retinal blood vessels.

In another aspect, by choosing other specific wavelengths of the emitter element, one can create output data maps showing oxygen content or concentrations of various substances, cells, or analytes across the fundus.

In another aspect, the time delay and/or phase shift between the illuminating beam pulse delivered by the emitter element and the detection of the acoustic signal by the detection element is used as a measure for the distance the acoustic wave has traveled. A longer time delay corresponds to the acoustic signal being generated by a structure further posterior; a shorter time delay indicates the originating structure being more anterior. The analysis element's processor may be programmed to use the distance information obtained at an area of interest to create a data output that is a three-dimensional representation of absorbance values. The analysis element's processor may also be programmed to filter the time delay/phase shift values in a way that only signals with similar time delays or phase shifts are processed, effectively limiting analysis or display to a single layer of the fundus. As an example, the processor may be programmed to differentiate absorbance signals originating from the retinal blood vessels near the surface of the retina from those originating from blood vessels in the choroid.

In another aspect, the analysis element's processor may be programmed to perform a frequency analysis of the digital acoustic wave signals. For example, frequency analysis can be performed by Fourier transformation or wavelet transformation of the detected signal. These transformations break up the time resolved acoustic signal into a spectrum of discrete frequencies and their relative signal strengths that are characteristic of certain molecules and substances.

The analysis element's processor may be programmed to combine two or more parameters from the group of: patient age, patient gender, date and time of measurement, emitter element wavelength, emitter element pulse duration, emitter beam energy, wave amplitude, time delay, phase shift, and frequency analysis. The combination of the parameters may be made by a neural network or mathematical algorithm and may be used to identify and/or determine the concentration of glucose, hemoglobin, glycated hemoglobin HbA1c, cholesterol, albumin, and/or other analytes in ocular blood vessels. The data output may be in the form of a glucose concentration number, a HbA1c concentration number, a total hemoglobin concentration number, a concentration number of another analyte, or a graphical representation of said concentration numbers versus time.

The data output may be transmitted from the analysis element to the display element 56 directly or indirectly by wire, storage media, wireless or through the internet. The display element may or may not be a physical part of the apparatus. It may be comprised of a monitor, alpha-numeric display, printer, smart phone, loudspeaker, or earphone to create the data output in visual or audible form. The display element may also communicate instructions and feedback to the user, patient and/or operator. The display element may be embodied by a combination of the emitter element and the transition element, where one of the light sources of the emitter element is visible and is intensity-modulated while being rapidly guided across the patient's fundus through the transition element, therefore allowing for direct projection of visible data output and/or instructions onto the patient's retina. Projected instructions may include alignment and registration marks to help the patient align him/herself with the apparatus.

The data output may be printed on an external or internal printer, stored on an external or internal storage device, for example solid state memory or hard disk drive, or may be transmitted from the analysis element to a therapeutic device, for example to an insulin pump.

The invention further relates to an apparatus configured to photoacoustically image and measure a structure at the human eye fundus comprising an emitter element for emitting electro-magnetic radiation, a transition element for delivering the electro-magnetic radiation into an eye, a detection element for detecting an acoustic wave and converting the acoustic wave into a digital wave signal, an analysis element for processing the digital wave signal into an image or measurement or both, and a display element for displaying a representation of the image and/or the measurement. The transition element is configured to guide the illumination beam into the eye, and the emitter element is configured to modulate the intensity of the illumination beam in order to project target information and/or text information and/or image information onto the retina of the eye.

Further advantageous measures and preferred apparatus embodiments result from the dependent claims.

The invention further relates to a process to photoacoustically image and measure structures at the human eye fundus, in particular carried out with an apparatus comprising (i) a emitter step to emit electro-magnetic radiation,
(ii) a transition step to deliver the electro-magnetic radiation into an eye,
(iii) a detection step to detect an acoustic wave and to convert the acoustic wave into a digital wave signal,
(iv) an analysis step to process the digital wave signal into an image or a measurement or both, and
(v) a display step to display a representation of the image and/or measurement. The process additionally comprises
(vi) a coupling step that acoustically couples the eye to a detection element such that the acoustic wave generated within the eye is guided onto the detection element.

Further advantageous measures and preferred process embodiments result from the claims. The process in accordance with the invention can be carried out using the apparatus described herein.

BRIEF DESCRIPTION OF THE DRAWINGS

In the following, the present invention will be described with reference to the accompanying exemplary, schematic drawings, in which.

DETAILED DESCRIPTION OF THE PREFERRED EMBODIMENT

Figure 1:
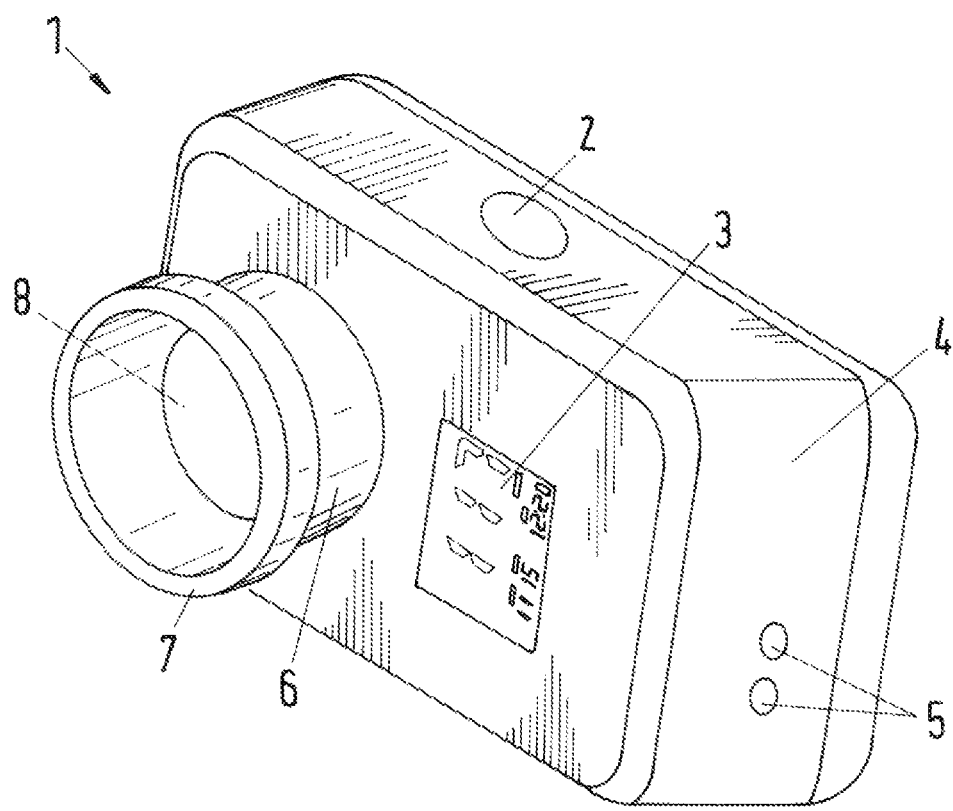
FIG. 1 is a top perspective of a photoacoustic fundus imaging and measuring device according to one embodiment.

Referring to FIG. 1, one embodiment of the photoacoustic fundus imaging and measuring device is depicted in the form of a handheld glucosetester (apparatus 1). From an external view, apparatus 1 consists of a housing 4 that contains the optical components, electronic components including controller and storage device, power switch, battery, and various device interfaces 5 to connect the glucosetester device by wire or wireless with peripheral equipment like printers, computers, internet, charging stations, or therapeutic devices like insulin pumps. The housing also contains a liquid crystal display (LCD) 3 that displays instructions and data to the user.

Figure 4:
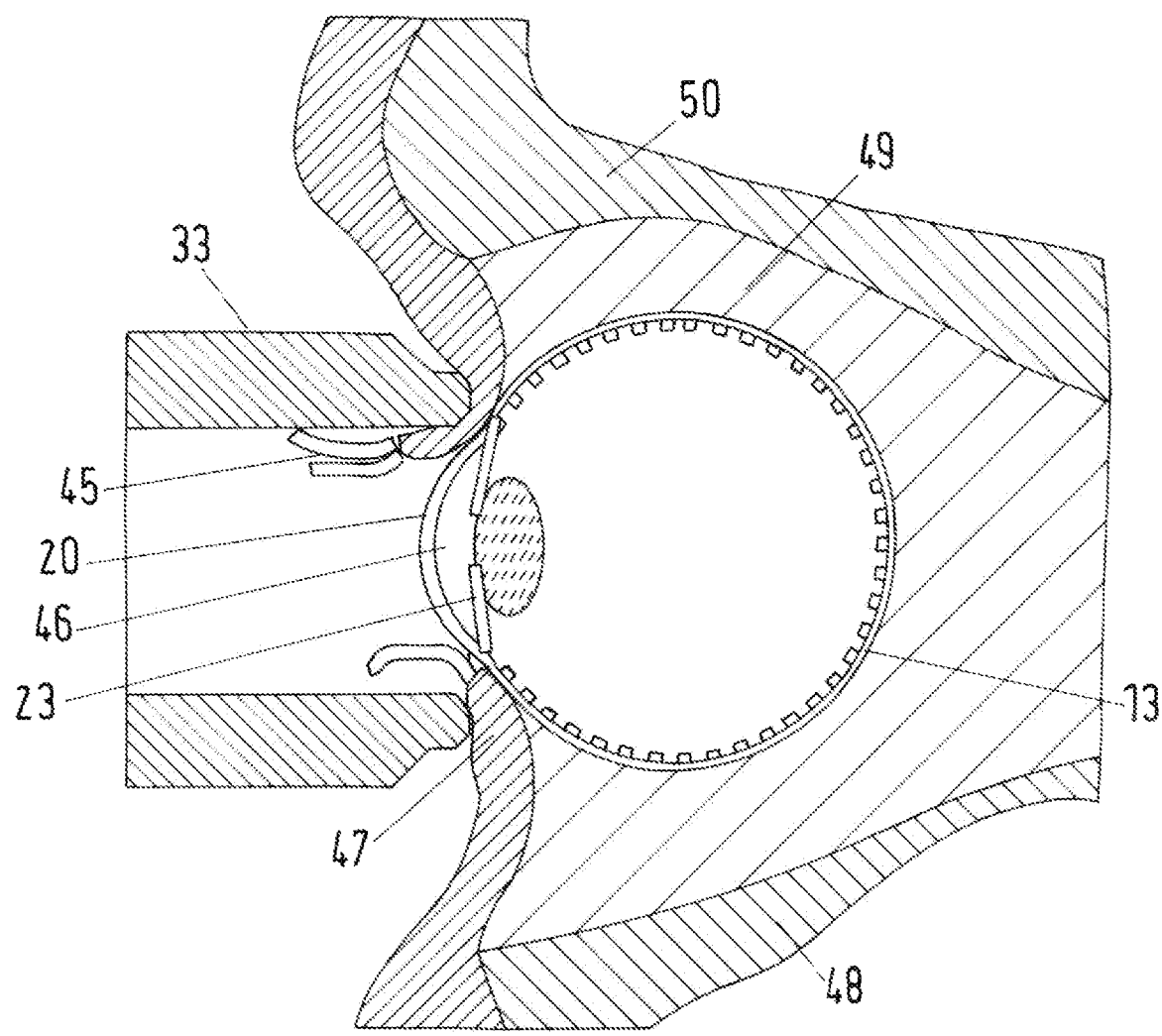
FIG. 4 is a schematic view of an eye in the eye socket.
Figure 5:
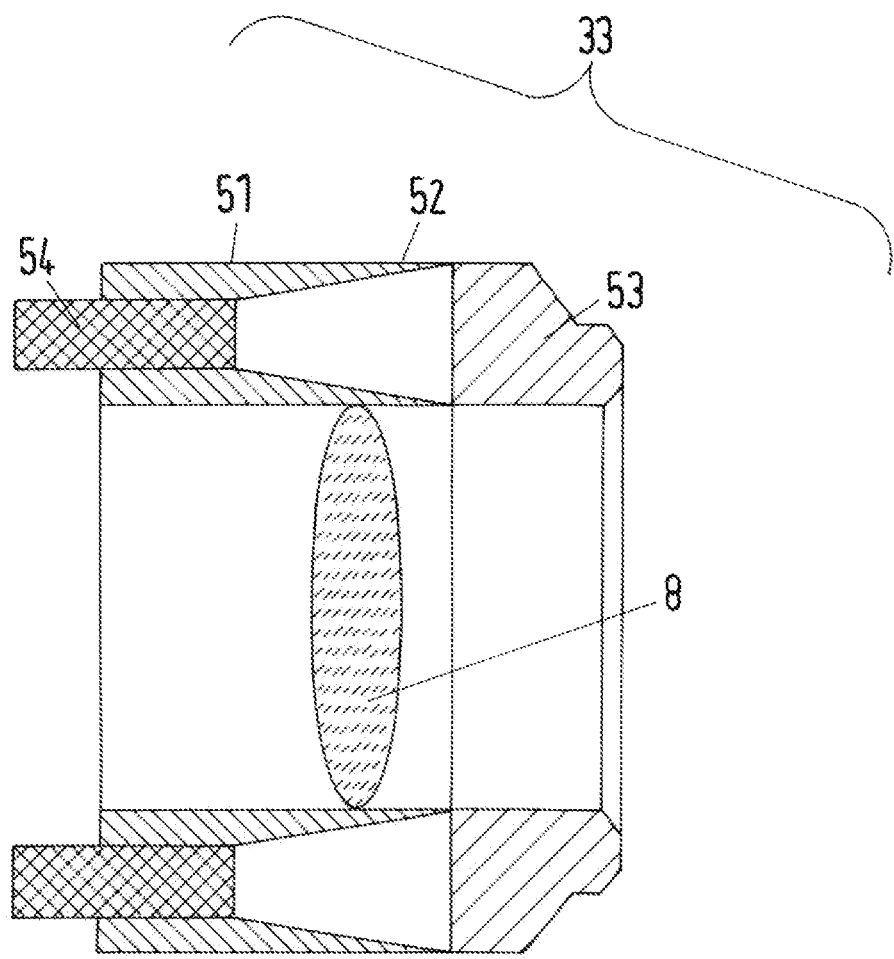
FIG. 5 is a cross sectional view of a coupling member according to an embodiment.
Figure 6:
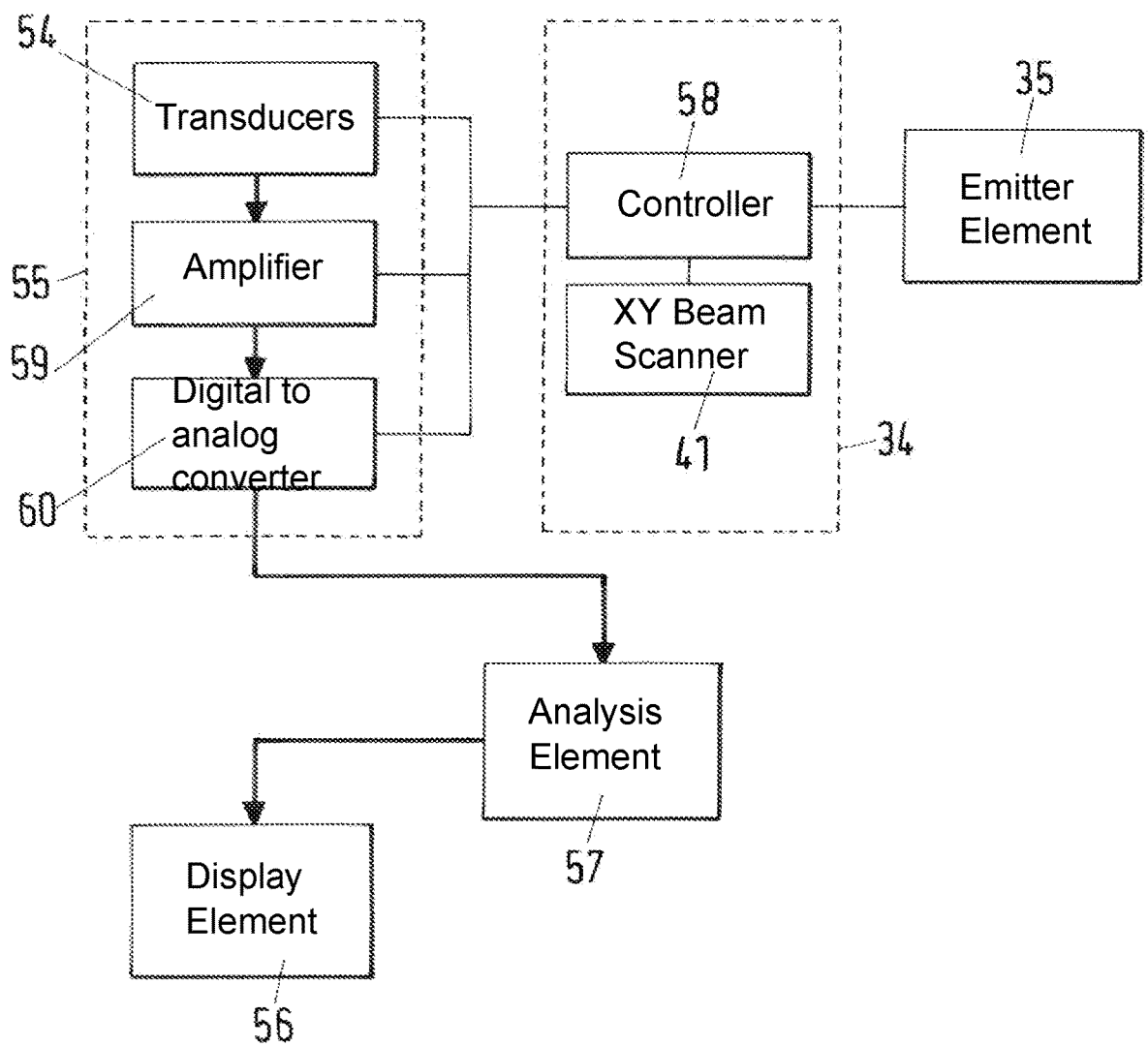
FIG. 6 schematically illustrates an emitter element 33, a transition element 34, a detection element 55, an analysis element 57 and a display element 56.

Before use, the user removes the disposable eyelid contact piece 7 (53) from its packaging container and pushes it onto the device's coupling member body 6 (51). The eyelid contact piece 7 is made of a cross-linked hydrophilic polymer and is stored in an aqueous solution to maximize its water content. Due to the large water content, the acoustic impedance of the eyelid contact piece is similar to that of living tissue. After the eyelid contact piece is mounted and the device is powered on, the device is held by the user such that the eyelid contact piece of the device's coupling member presses against the upper and lower eyelids 45, 47 of the user's eye as shown schematically in FIG. 4. Also, as shown in FIG. 4, the maxilla 48, orbital fat 49 and frontal bone 50 surround the eye. While holding the device in this position, the user looks through the objective lens 8 (FIG. 5) into the device.

Figure 3:
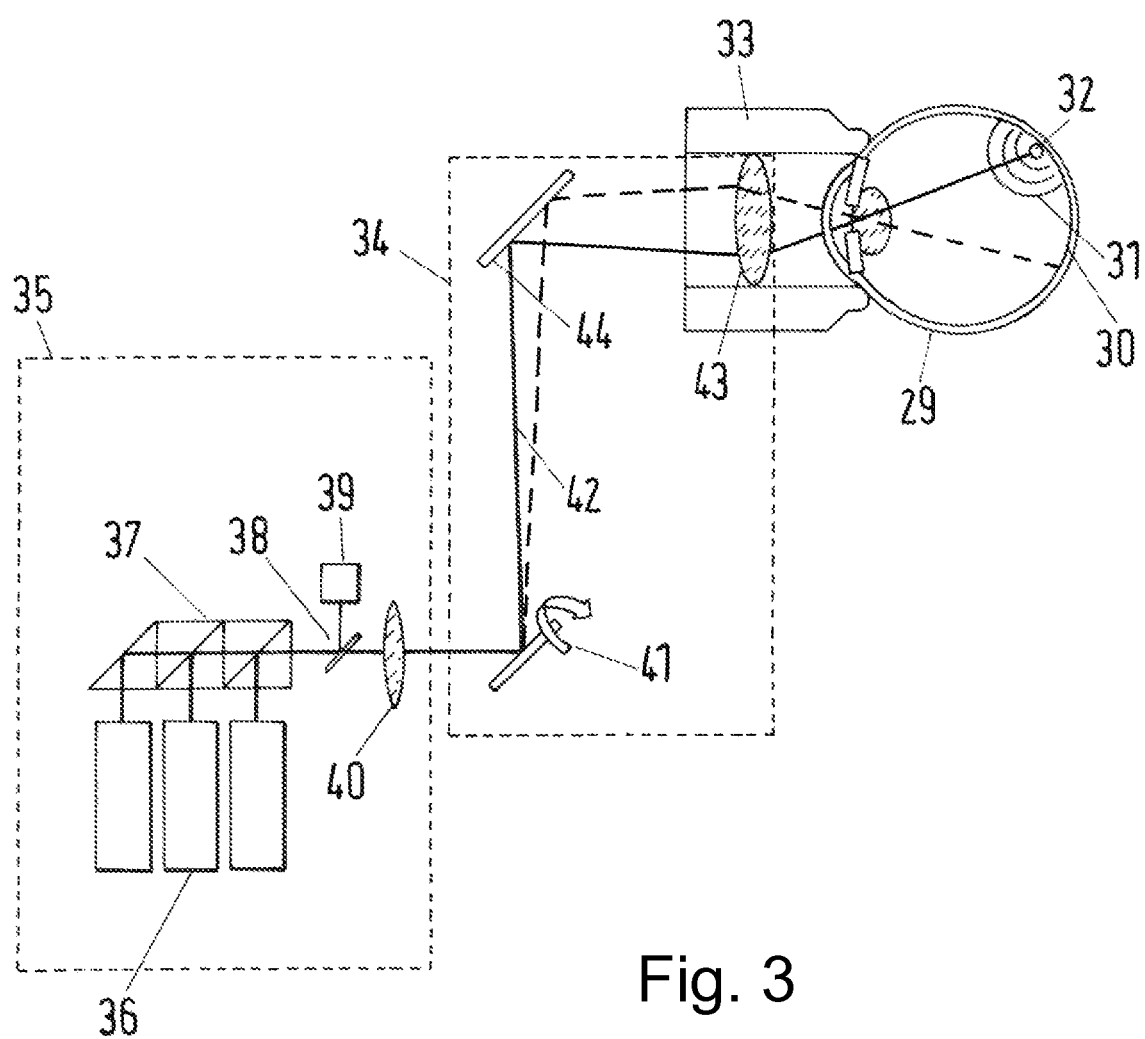
FIG. 3 is schematic view of an emitter element and a transition element 34 according to one embodiment.

As best seen in FIG. 3, the emitter element 35 in this embodiment includes three diode lasers 36, each of which contains beam shaping optics to form a collimated beam of about 1 mm diameter. The wavelengths of the diode lasers were chosen to be 830 nm, 905 nm, and 1060 nm, although other wavelengths may be chosen. A beam combiner 37 consisting of an array of prisms with dichroic coatings combines the three collimated laser diode beams into one coaxial illuminating beam 42. The beam splitter 38 reflects a small percentage of the coaxial illuminating beam onto a photo detector 39 to measure the energy of the illuminating beam and to create a trigger signal from each pulse. The majority of the illuminating beam passes through the beam splitter 38 and is focused by the focusing lens 40 onto the front focal plane of the objective lens 43 in the coupling member 33. On its path to the objective lens, the converging illuminating beam 42 is reflected off the XY beam scanner 41 (including folding mirror 44) which deflects the beam horizontally and vertically according to voltages received from the controller circuit 58. In the preferred embodiment, the XY beam scanner is a microelectromechanical (MEMS) mirror which deflects the illuminating beam in the form of a raster scan pattern of 256 lines of 256 points each. The horizontal line frequency is approximately 100 Hz, which results in a data acquisition time for a full field of 256 by 256 points of approximately 2.5 seconds. Other beam scanners like galvanometer scanners, resonant scanners, photoacoustic scanners, or rotating scanners may be used. Other deflection or scan patterns, number of lines, points per line, or frequencies may be chosen; for example, a scan pattern of one or more concentric circles may provide a sufficient number of data points and may reduce the data acquisition time.

At each point of the scan pattern, the deflected illuminating beam travels towards the objective lens which serves the dual purpose of collimating the illuminating beam and imaging the mirror surface of the XY beam scanner onto the pupil 46 of the user's eye 29. In this configuration, the illuminating beam always passes through the user's pupil regardless of the amount of deflection by the XY beam scanner. While entering the eye, the illuminating beam is focused by the cornea 20 and the lens 22 onto the area of interest 32 at the eye fundus 30, the location of which is determined by the horizontal and vertical deflection caused by the XY beam scanner.

During the alignment phase, only the 830 nm laser diode is turned on so that the user can see a dimly lit scan pattern on the retina to serve as alignment target. While holding the device with its eyelid contact piece against the upper and lower eyelid, the user moves the device horizontally and vertically until the scan pattern on the retina is seen without any vignetting. When ready, the user pushes the push button 2 to start the data acquisition. The 830 nm laser diode may be intensity modulated to project alignment target information, text information, or image information onto the user's retina. Other wavelengths and/or additional light sources may be used for the purpose of projecting information onto the user's retina.

Figure 2A:
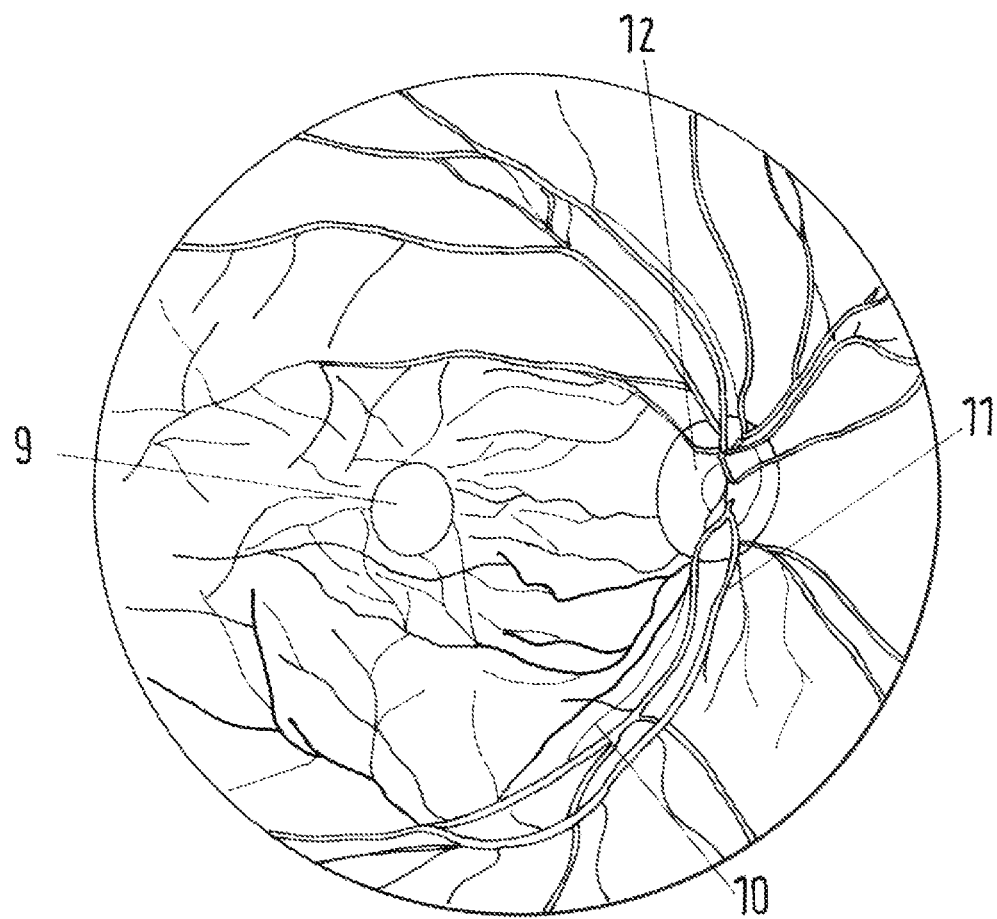
FIG. 2A is a schematic view of the fundus of the eye.
Figure 2B:
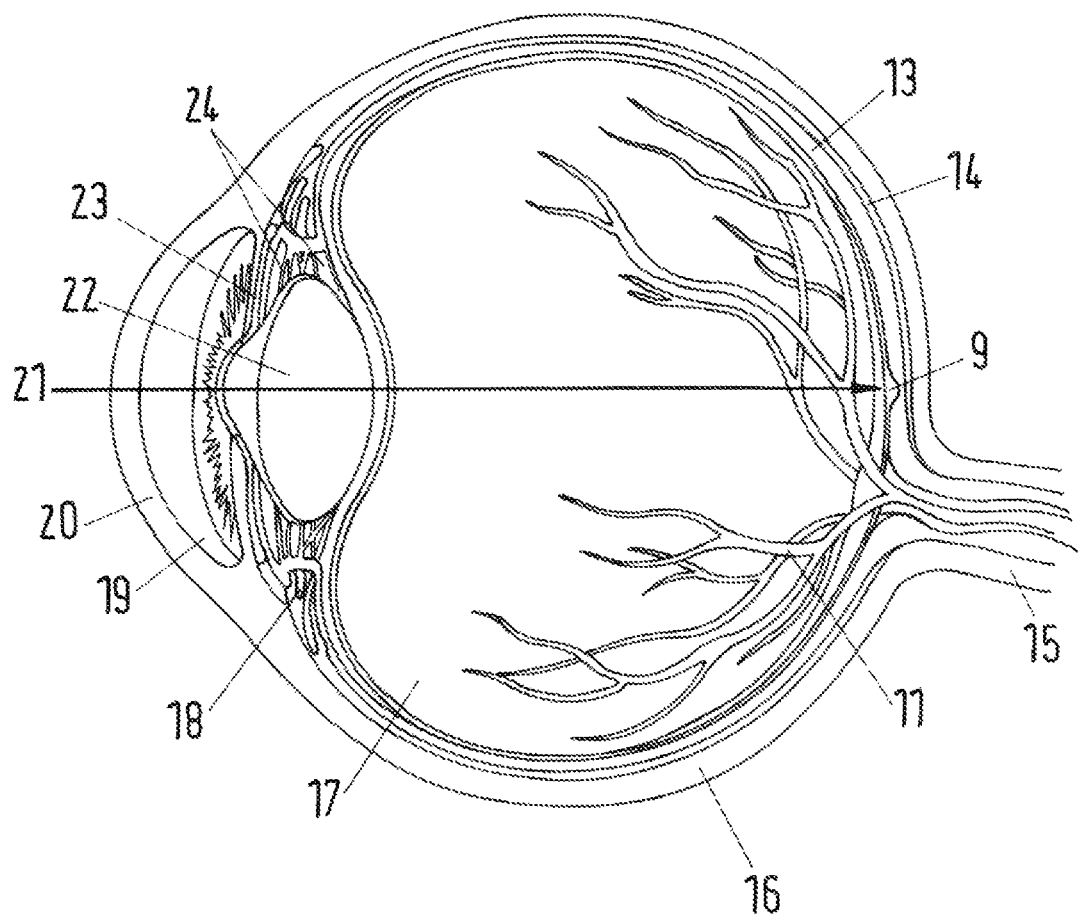
FIG. 2B is a cross sectional view of the eye.
Figure 2C:
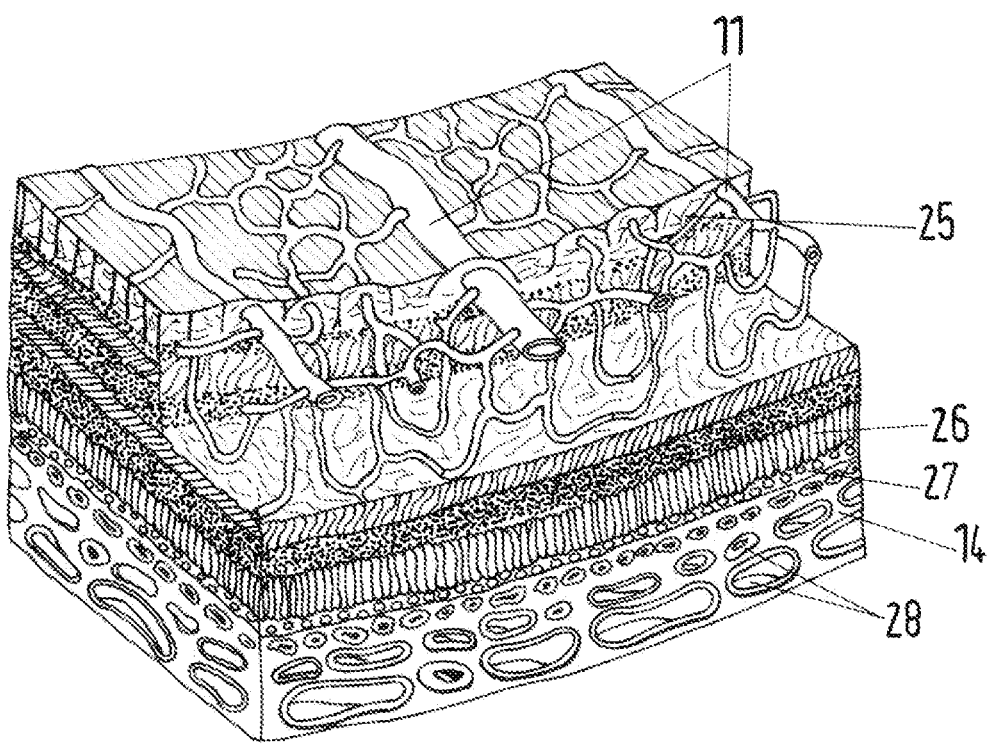
FIG. 2C is sectional view of the fundus.
Figure 7:
FIG. 7 schematically shows data acquisition.
Figure 8:
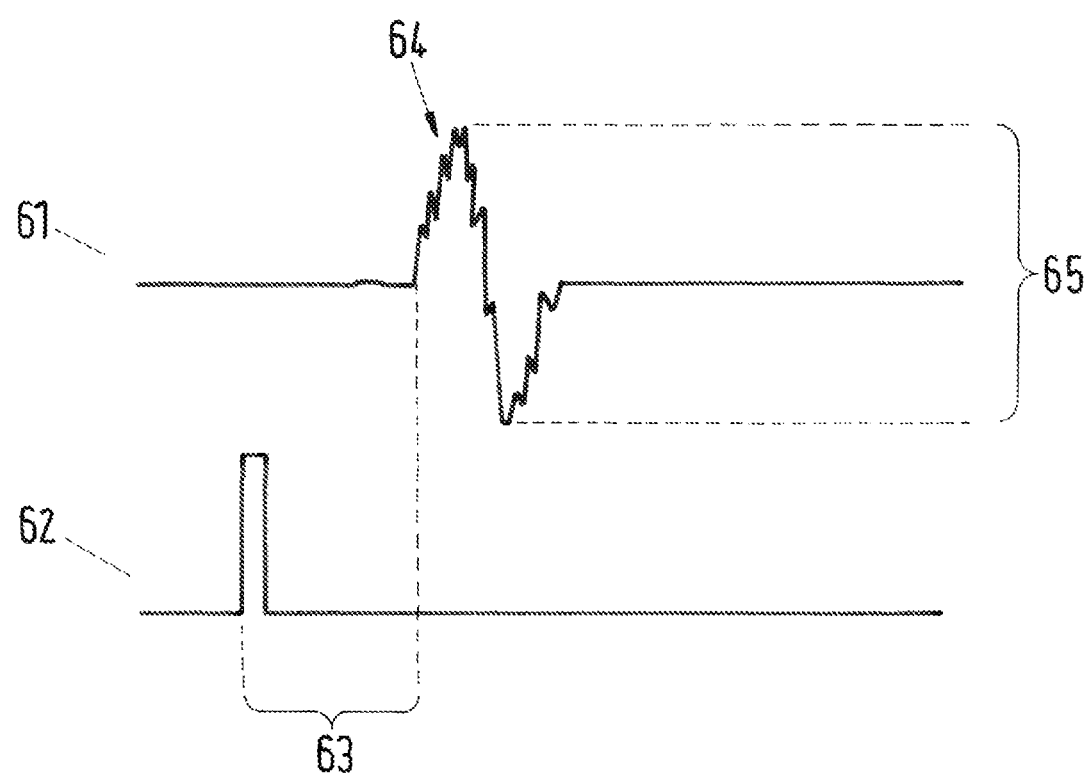
FIG. 8 schematically shows an acoustic wave signal and a laser pulse.
Figure 9A:
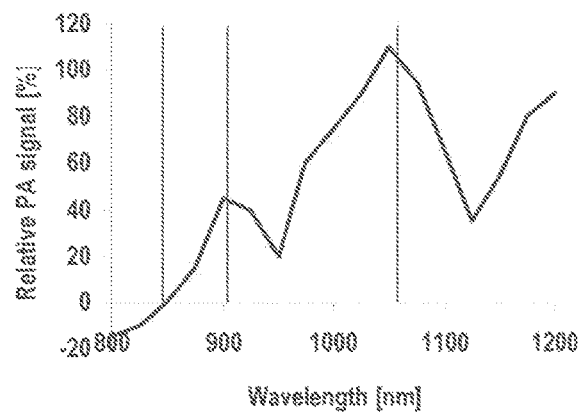
FIGS. 9A-9D illustrate different analytes with different absorption spectra.
Figure 9B:
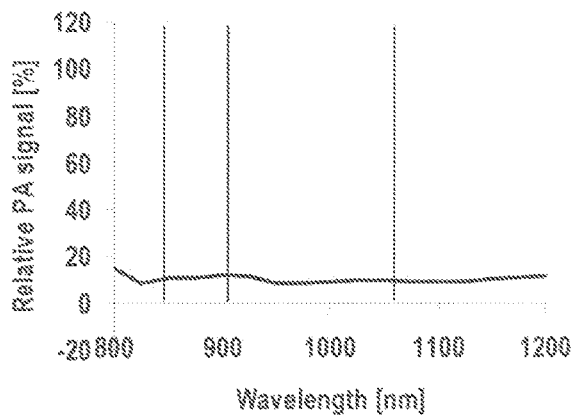
Figure 9C:
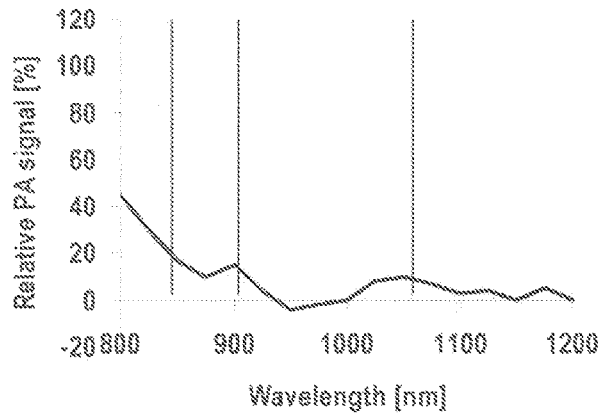
Figure 9D:
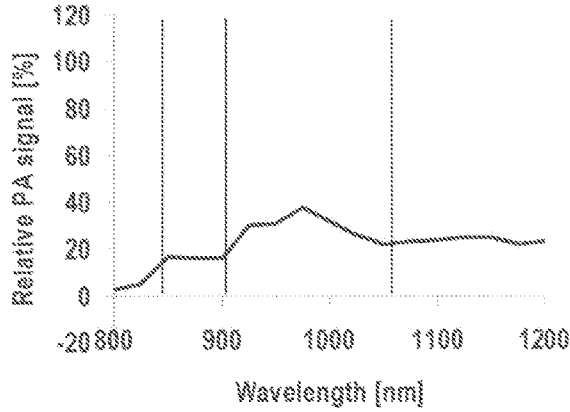

During data acquisition, as schematically shown in FIGS. 7 and 8, at each point of interest the three laser diodes are pulsed (i.e., laser pulse 62) sequentially with a pulse width of approximately 0.2 microseconds and a time delay 63 of approximately 15 microseconds between the pulses of any two laser diodes before the illuminating beam is deflected to the next point of interest. The pulsed illuminating beam penetrates the eye fundus 30 and is simultaneously absorbed by a multitude of layers and components of the eye 29 and the eye fundus along its path, including the fovea 9, the nerve fibers 10, the optic nerve head 12, optic nerve 15, the cornea 20, aqueous humor 19, lens 22, iris 23, zonule fibers 24, nerve fiber layer 25, rod and cone layer 26, Retinal pigment epithelium layer 27, vitreous humor 17, ciliary muscle 18, retinal blood vessels 11 and the blood therein, the retina 13, the choroid 14, the choroidal blood vessels 28 and the blood therein, and the sclera 16 as shown in FIGS. 2A, 2B and 2C. FIG. 2B illustrates the direction of light 21.

Each absorption event at any of the layers and components of the eye causes an acoustic wave 31 to emanate from the respective absorber, which travels through the eye with the speed of sound of approximately 1500 m/s. Due to the physical path difference of approximately 23 mm between the cornea and the fundus, acoustic waves emanating from the retinal blood vessels lag behind the acoustic waves emanating from the cornea and lens by approximately 15 microseconds. Acoustic waves emanating from choroidal blood vessels lag behind the acoustic waves emanating from the retinal blood vessels by approximately 0.6 microseconds.

Referring to FIGS. 2, 4, 5 and 6, the acoustic waves reach the boundaries of the eye and pass through the sclera 16, the orbital fat 49 and the upper and lower eye lids 45, 47 where they penetrate into the eyelid contact piece 7 of the device. Acoustic lenses 52 molded into the coupling member body 6 funnel the acoustic waves onto two piezo-electric transducers 54 that have a detection bandwidth of approximately 30 MHz. The resulting electric signals are amplified by an amplifier 59, digitized by an analog-to-digital converter 60 with a digitizing speed of approximately 100 Ms/s, and processed by the processor of the analysis element 57. It should be obvious that one or more than two transducers may be used, and that the sampling frequency and detection bandwidth may be chosen differently.

Figure 10:
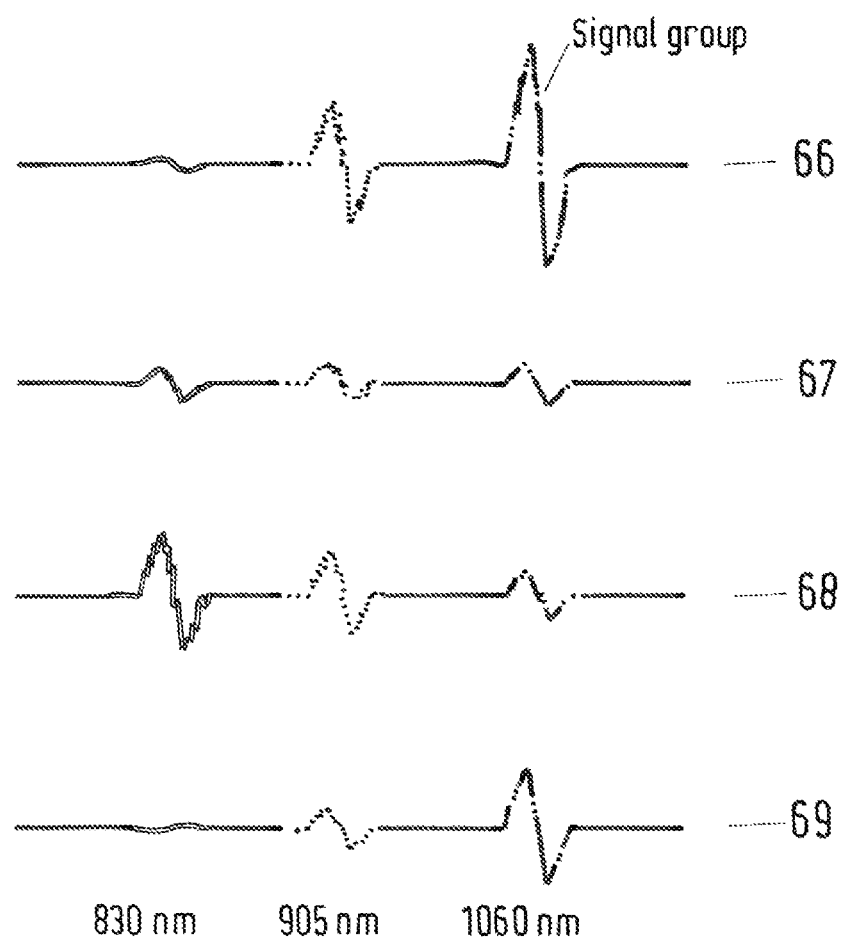
FIG. 10 illustrates acoustic signals resulting from sequential pulsing of the three wavelength laser diodes.

As can be seen in FIGS. 9A-9D, different analytes have different absorption spectra and, therefore, create different acoustic wave signal strengths at a given wavelength. Shown in FIGS. 9A, B, C, and D are the relative photoacoustic signal strengths resulting from the blood analytes glucose 66, cholesterol 67, albumin 68, and sodium chloride 69, respectively. Highlighted in each FIGS. 9A-9D are the wavelengths of 830 nm, 905 nm, and 1060 nm used in the preferred embodiment. Referring to FIGS. 7 and 10, the acoustic signals 61 resulting from sequential pulsing of the three wavelength laser diodes show three distinct signal groups, whereby the amplitude differences between the groups is characteristic for the analyte emitting the acoustic wave, and the absolute amplitude is a measure for the amount of absorption and, therefore, the concentration of a given blood analyte.

Using different wavelengths and/or additional wavelengths, other or additional substances or blood components may be measured; for example hemoglobin or glycated hemoglobin HbA1c concentration in the blood may preferably be measured at a wavelength of about 532 nm.

Figure 11:
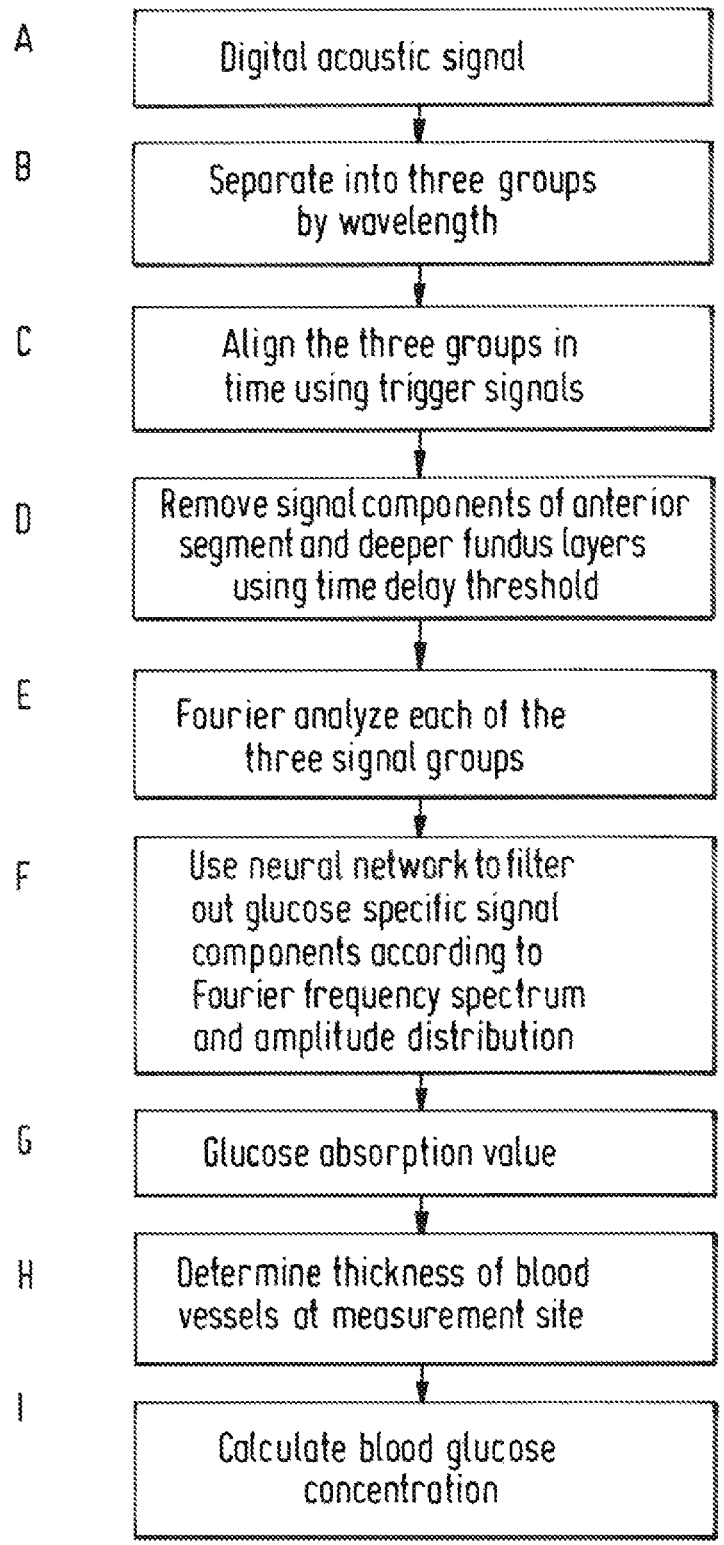
FIG. 11 illustrates a flow diagram of the data analysis.
Figure 13:
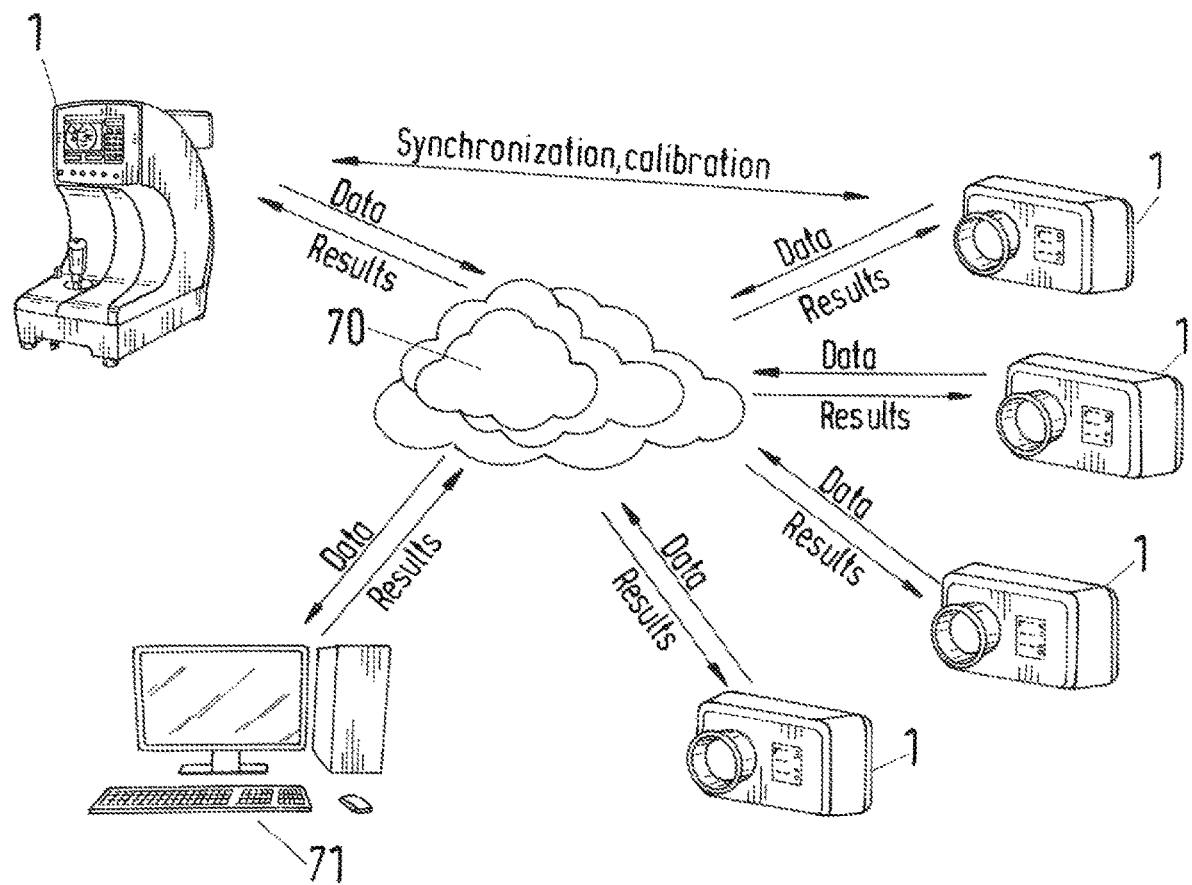
FIG. 13 is a schematic view in which a plurality of handheld glucosetester devices are connected through the internet with a remote analysis element.

FIG. 11 depicts a flow diagram of the data analysis. In the preferred embodiment of a handheld glucosetester, data analysis of steps A to D in FIG. 11 are performed by the controller in the handheld device. The intermediate results of step D are transmitted by wireless data transmission to a remote analysis element 71 as schematically shown in FIG. 13. The processor of the remote analysis element performs steps E to I of FIG. 11 and transmits the resulting glucose concentration data back to the handheld glucosetester 1 where they are displayed on the LCD display 3 and stored on the device's storage device.

Alternate Embodiments of the Invention

Figure 12A:
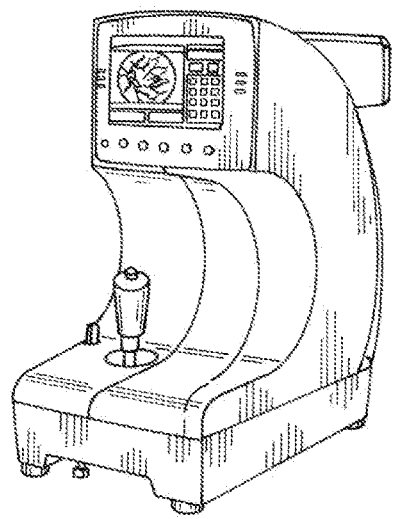
FIG. 12A is a perspective view of a photoacoustic fundus imaging and measuring device as a stationary device.

Referring to FIG. 12A, an embodiment is shown where the photoacoustic fundus imaging and measuring device is configured as a stationary device and where the alignment of the device to the patient's eye under examination is performed by an operator different from the user or patient.

Figure 12B:
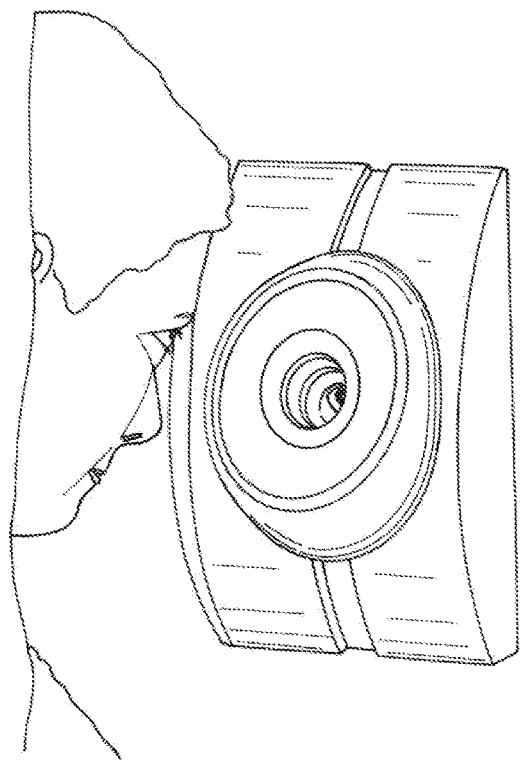
FIG. 12B is a perspective view of an alternate embodiment of the photoacoustic fundus imaging and measuring device as a stationary device.

FIG. 12B shows an alternate embodiment of the photoacoustic fundus imaging and measuring device where the device is configured as a stationary device and where the users or patients perform the alignment and measurement themselves.

FIG. 13 depicts an embodiment where a plurality of handheld glucosetester devices are connected through the internet 70 with a remote analysis element 71 and/or with one or more stationary device. In this embodiment, the stationary devices may be located at practitioners' offices and are configured according to FIG. 12A or 12B and may be configured to measure the HbA1c concentration in the blood. A patient or user using a handheld glucosetester according to the preferred embodiment of this invention may use the handheld glucosetester several times per day to determine the short term variation of the blood glucose concentration while he or she may visit the practitioner approximately every three month to get the HbA1c concentration measured with a device according to the embodiments of FIG. 12A or 12B. At each visit at the practitioner's office the handheld glucosetester may synchronize its stored data with the practitioner's device, so that the handheld glucosetester may be re-calibrated, and the practitioner may glean information on both long and short term fluctuations of the patient's blood glucose concentration.

Figure 14:
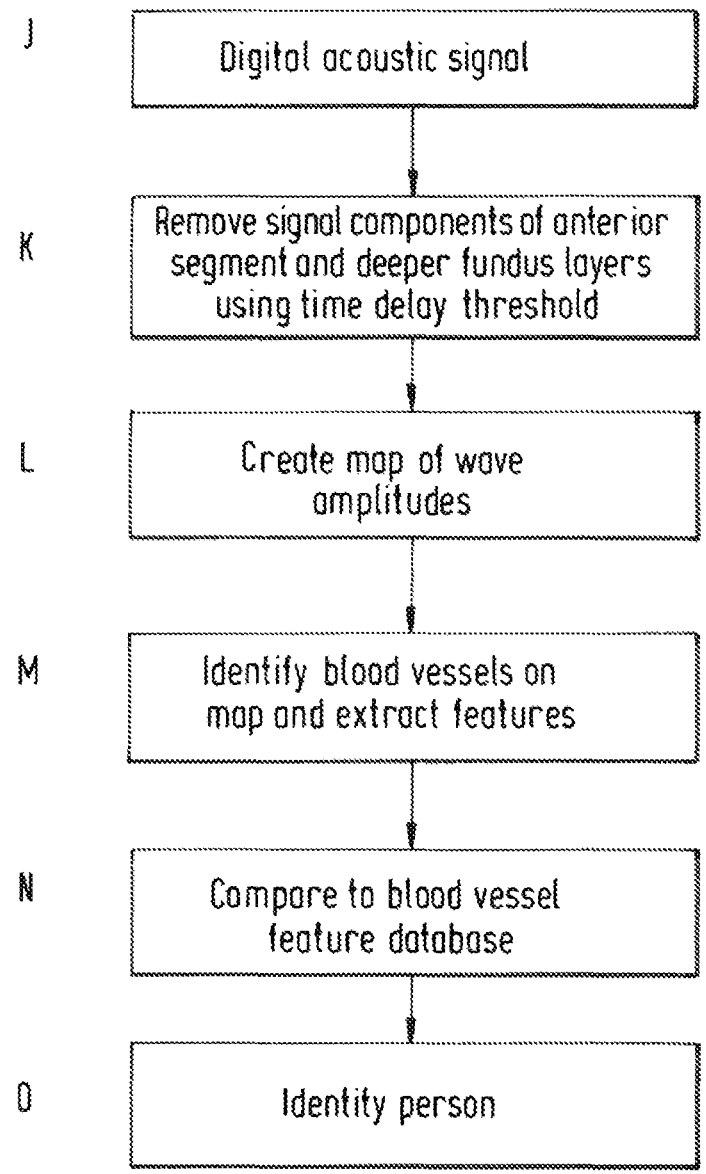
FIG. 14 is a procedure in which resulting retinal blood vessel map is analyzed to search and identify unique features and landmarks.

In another embodiment of the photoacoustic fundus imaging and measuring device, the device is used as a device for identifying persons. In this embodiment, one laser diode is used with a wavelength of 532 nm. Other light sources emitting at a wavelength where hemoglobin shows high absorption may be used. Referring to FIGS. 8 and 14, the wave amplitude 65 of the acoustic wave generated at each point of interest targeted by the scan pattern is determined by the analysis element and stored as a two-dimensional map of data. Since hemoglobin is located within the blood vessels and the wave amplitude is a measure for the rate of absorption, areas on the data map showing high wave amplitudes correspond to retinal blood vessels. The resulting retinal blood vessel map is further analyzed as per FIG. 14 to search and identify unique features and landmarks, for example characteristic branches of blood vessels. The features and landmarks are then compared to a database of known features and landmarks in the retinal blood vessel maps of known persons in order to find the best match and identify a person.

Since the photoacoustic fundus imaging and measuring device creates a retinal blood vessel map based on acoustic signals, the quality of person identification is not affected by optical noise and/or reflections and/or environmental lighting conditions as is the case with identification methods based on optical imaging.

The invention claimed is:

1. An apparatus configured to photoacoustically image and measure a structure at the human eye fundus, comprising:
   an emitter configured to emit electro-magnetic radiation;
   a transitioner configured to deliver the electro-magnetic radiation into an eye;
   a detector configured to detect an acoustic wave and convert the acoustic wave into a digital wave signal;
   an analyzer configured to process the digital wave signal into at least one of an image and a measurement;
   a display configured to display a representation of at least one of the image and the measurement; and
   a coupler configured and arranged to acoustically couple the eye to the detector such that the acoustic wave generated within the eye is capable of being guided onto the detector, the coupler comprising a coupler body, an objective lens, an eyelid contact piece, the coupler being tubular, made of an acoustically conducting material and configured to touch at least one of an upper eye lid and a lower eye lid of the eye while the eye is open when in use, and the objective lens being disposed centrally within the coupler and the detector being disposed radially outside and spaced from the objective lens,
   the detector being physically coupled to the coupler at a predetermined location.

2. The apparatus according to claim 1, wherein the emitter comprises one or more light sources configured to emit electro-magnetic radiation, as beams of different wavelengths, and a beam combiner configured to combine the beams of different wavelengths into one illumination beam.

3. The apparatus according to claim 1, wherein the coupler comprises an eyelid contact piece capable of being removed from a coupler body.

4. The apparatus according to claim 2, wherein the transitioner is configured to guide the illumination beam into the eye.

5. The apparatus according to claim 2, wherein the transitioner is configured to guide the illumination beam into the eye, and the emitter is configured to modulate the intensity of the illumination beam to project at least one of target information, text information and image information onto the retina of the eye.

6. The apparatus according to claim 1, wherein the transitioner comprises a microelectromechanical mirror scanner.

7. The apparatus according to claim 1, wherein the detector is mounted to or within the coupler.

8. The apparatus according to claim 1, wherein the detector comprises one or a plurality of acoustic sensors.

9. The apparatus according to claim 1, wherein the analyzer comprises an electronic processor configured to extract a measurement from the digitized acoustic wave signal.

10. The apparatus according to claim 1, wherein the analyzer is located at a physical location different from the physical location of the other elements of the apparatus.

11. The apparatus according to claim 1, wherein the display is located at a physical location different from the physical location of the other elements of the apparatus.

12. The apparatus according to claim 1, wherein the measurement comprises at least one of a wave amplitude, time delay, phase shift or a frequency component of the detected acoustic wave, and the measurement is capable of being used to create data output of the analyzer.

13. The apparatus according to claim 1, wherein the emitter is configured such that a wavelength can be chosen from a wavelength range where absorption by hemoglobin in the blood is at a peak.

14. The apparatus according to claim 1, wherein the emitter is configured such that a combination of a multitude of wavelengths can be chosen from a wavelength range where absorption by glucose in the blood produces a characteristic acoustic wave.

15. The apparatus according to claim 1, wherein the apparatus is a handheld device.

16. The apparatus according to claim 12 wherein the analyzer is configured such that the data output is transmitted to a therapeutic device.

17. An apparatus configured to photoacoustically image and measure a structure at the human eye fundus, comprising:
an emitter configured to emit electro-magnetic radiation;
a transitioner configured to deliver the electro-magnetic radiation into an eye;
a detector configured to detect an acoustic wave and converting the acoustic wave into a digital wave signal;
an analyzer configured to process the digital wave signal into at least one of an image or a measurement;
a display configured to display a representation of at least one of the image and the measurement, the transitioner being configured to guide the illumination beam into the eye, and the emitter being configured to modulate the intensity of the illumination beam to project at least one of target information, text information, and image information onto the retina of the eye; and
a coupler configured and arranged to acoustically couple the eye to the detector such that the acoustic wave generated within the eye is capable of being guided onto the detector, the coupler comprising a coupler body, an objective lens, an eyelid contact piece, the coupler being tubular made of an acoustically conducting material and configured to touch at least one of an upper eye lid and a lower eye lid of a patient's eye while the eye is open when in use, and the objective lens being disposed centrally within the coupler and the detector being disposed radially outside and spaced from the objective lens,
the detector being physically coupled to the coupler at a predetermined location.

18. A process to photoacoustically image and measure structures at the human eye fundus, carried out with an apparatus, comprising:
emitting electro-magnetic radiation;
delivering the electro-magnetic radiation into an eye;
detecting an acoustic wave and converting the acoustic wave into a digital wave signal;
processing the digital wave signal into at least one of an image and a measurement;
displaying a representation of at least one of the image and the measurement;
coupling the eye to a coupler, the coupler including a detector and an objective lens, the detector being physically coupled to the coupler at a predetermined location, and the objective lens being disposed centrally within the coupler and the detector being disposed radially outside and spaced from the objective lens,
the acoustically coupling including contacting at least one of the upper eye lid and a lower eye lid of the eye with a tubular structure made of an acoustically conducting material while the eye is open.

19. The process of claim 18, wherein the emitting comprises the emission of one or more electro-magnetic radiation beams.

20. The apparatus according to claim 7, wherein
the detector includes a piezo-electric transducer, an amplifier, and a converter, and the acoustic lens is configured to funnel the acoustic wave onto the piezo-electric transducer which is in communication with the amplifier, the amplifier is configured to amplify the acoustic wave, and the converter is configured to convert the amplified acoustic wave to the digital wave signal to be processed by the analyzer.

21. The apparatus according to claim 1, wherein
the coupler comprises an acoustic lens configured to funnel the acoustic wave onto the detector.

22. The apparatus according to claim 1, wherein
the detector and the acoustic lens are disposed in a peripheral position of the coupler body such that both the detector and the acoustic lens are disposed radially outside and spaced from the objective lens.

23. The apparatus according to claim 17, wherein
the coupler comprises an acoustic lens configured to funnel the acoustic wave onto the detector.

24. The apparatus according to claim 23, wherein
the detector and the acoustic lens are disposed in a peripheral position of the coupler body are disposed radially outside and spaced from the objective lens.

25. The process according to claim 18, wherein
the acoustic wave generated within the eye is funneled onto the detector by an acoustic lens.

26. The process according to claim 25, wherein
the detector and the acoustic lens are disposed in a peripheral position of the coupler body are disposed radially outside and spaced from the objective lens.

* * * * *